(12) United States Patent
Shikata et al.

(10) Patent No.: US 6,169,046 B1
(45) Date of Patent: Jan. 2, 2001

(54) ABSORBABLE BARRIER MEMBRANE

(75) Inventors: Toshiki Shikata, Sakura; Yasutoshi Kakizawa, Toyonaka; Jyunzo Tanaka; Yasushi Suetsugu, both of Tsukuba; Masanori Kikuchi, Nagareyama; Hiroo Miyairi; Kazuo Takakuda, both of Tokyo; Yoshihisa Koyama, Kawasaki, all of (JP)

(73) Assignee: Director-General of National Institute for Research in Organic Materials, Tsukuba (JP)

(*) Notice: Under 35 U.S.C. 154(b), the term of this patent shall be extended for 0 days.

(21) Appl. No.: 09/044,162

(22) Filed: Mar. 19, 1998

Related U.S. Application Data

(63) Continuation-in-part of application No. 08/712,994, filed on Sep. 10, 1996, now Pat. No. 5,844,066.

(30) Foreign Application Priority Data

Mar. 25, 1997 (JP) .................................................. 9-072475
Jan. 14, 1998 (JP) .................................................. 10-006120

(51) Int. Cl.[7] .............................. D04H 1/00; D04H 3/00
(52) U.S. Cl. ........................ 442/361; 442/365; 442/414
(58) Field of Search .................................. 442/361, 365, 442/414; 606/230; 433/215; 424/423

(56) References Cited

U.S. PATENT DOCUMENTS

| | | | |
|---|---|---|---|
| 4,961,707 | * 10/1990 | Magnusson et al. | ............ 433/215 |
| 5,676,699 | * 10/1997 | Gogolewski et al. | ............ 623/16 |
| 5,844,066 | * 12/1998 | Kakizawa | ............ 528/354 |

FOREIGN PATENT DOCUMENTS

| 10000229 | * | 1/1998 | (JP) . |
| 10036651 | * | 2/1998 | (JP) . |

OTHER PUBLICATIONS

Grant, Grant and Hackh's Chemical Dictionary, McGraw Hill, p. 106, 1987.*

* cited by examiner

Primary Examiner—Newton Edwards
(74) Attorney, Agent, or Firm—Armstrong, Westerman, Hattori, McLeland & Naughton

(57) ABSTRACT

The present invention provides an absorbable barrier membrane for guided tissue regeneration which is useful for regeneration of animal tissues, including those of humans, the absorbable barrier membrane being superior in heat stability, processability, reproducibility, storage stability, bioabsorbablity, and tissue regeneration effects, and further provides a method for regeneration, using the absorbable barrier membrane, of a mandible, periodontal tissue, or defective tubulous bone, and particularly a defective tubulous bone which possesses a segmental bone defect in which both ends of the bone are in separate segments. The above objects are attained by an absorbable barrier membrane for use in guided tissue generation, comprising a lactic copolyester in which a polymerization catalyst is deactivated, as an essential component.

12 Claims, 3 Drawing Sheets

ABSORBABLE BARRIER MEMBRANE

This application is a Continuation-In-Part of application Ser. No. 08/712,994, filed Sep. 10, 1996, new U.S. Pat. No. 5,844,066.

BACKGROUND OF THE INVENTION

1. Field of the Invention

The present invention relates to an absorbable barrier membrane for use in guided tissue regeneration which is useful for regeneration of tissues of animals, including humans, and to a method for regeneration, using the absorbable barrier membrane, of a mandible, periodontal tissue, or defective tubulous bone, and particularly a defective tubulous bone which possesses a segmental bone defect in which both ends of the bone are in separate segments.

2. Description of Related Art

As methods for regeneration of bone, methods for filling or implantation of an absorbable cement or a sintered calcium phosphate as an absorbable ceramic has been known, in addition to guided tissue regeneration. Numerous patent publications and other literature exist with respect to these methods.

Japanese Language Publication (Kohyo), No. Hei 1-501289, corresponding to PCT Patent Application discloses a biological composite material containing contiguous pores, comprising a polymer and ceramics, and polylactic acid and calcium phosphate are disclosed as examples of the polymer and ceramics. An increase in alveolar protuberance is also disclosed. However, there is no apparent description about guided tissue regeneration. Also, there is no description about deactivation of a polymerization catalyst of the polymer.

Extensive literature exists regarding guided tissue regeneration in dentistry, and are disclosed in detail in "GTR No Kagaku To Rinsho (Science and Clinical Studies of GTR)", written by Nakamura and Uraguchi, published by Quintessence Shuppan, Japan.

In particular, regeneration of the periodontal tissue for treating a periodontal disease is performed by preventing invasion of gum into the space at which the periodontal tissue should be regenerated, using a barrier membrane. As the barrier membrane, an unabsorbable polytetrafluoroethylene is mainly used. However, an unabsorbable membrane of polytetrafluoroethylene or the like has a drawback in that the burden on the patient is large because a surgery must be conducted in order to remove the membrane after the tissue is regenerated.

On the other hand, as the absorbable material, polylactic acid, a copolymer of lactic acid and glycolic acid, and the like have been reported. For example, Japanese Patent Publication, First Publication, No. Hei 2-63465 discloses a lactic copolyester such as a copolymer of lactic acid and ε-caprolactone, as a material for regeneration of periodontal tissue. However, there was a drawback in that the material is liable to deteriorate particularly during melt-molding because the polymerization catalyst is not deactivated. In addition, Japanese Patent Publication, First Publication, No. Hei 7-498 discloses a mixture of a piezoelectric polymer substance and inorganic micro particles. However, calcium phosphate was not described as an example of the inorganic micro particles and deactivation of the polymerization catalyst of the lactic polymer was not described.

Ossification includes membranous ossification and cartilaginous ossification. It is known that the cranium, mandible, clavicle, etc., are formed by membranous ossification, whereas tubulous bone (e.g., the humerus, femur, tibia, fibula, carpus, ulna, etc.) is formed by cartilaginous ossification. Regeneration of bone by guided tissue regeneration has been studied with respect to the mandible, mainly, and application of guided tissue regeneration to the tubulous bone formed by cartilaginous ossification has rarely been performed.

As an application of guided tissue regeneration to tubulous bone, application to an epiphysis defect is described in Japanese Patent Publication, First Publication, No. Hei 7-236688; however, this bone defect is not in segmented form.

Examples of use in segmented tubulous bone are disclosed in a study by Farso-Nielsen, et al., (Journal of Dental Research (special issue), Vol. 70, page 577, 1991) and a study by Lu Shibi, et al., (Chinese Medical Journal, Vol. 109, No. 7, pages 551 to 554). In the case of Farso-Nielsen, et al., a test using an absorbable polyurethane membrane was performed. However, since sufficient regeneration of bone cannot be performed by only using the membrane, decalcified bone must be used in combination. In the case of Lu Shibi, et al., since an unabsorbable silicone membrane is used, the membrane must be removed after regeneration of the bone.

As guided tissue regeneration for regeneration and bridging of a severed peripheral nerve, use of a tube of polyglycolic acid is known. For example, Japanese Language Publication (Kohyo), No. Hei 1-503204, corresponding to PCT Patent Application discloses mainly a device for nerve regeneration; however, there is a drawback in that the device is liable to degrade during molding because the polymerization catalyst is not deactivated.

That is, conventional bioabsorbable membrane of polylactic acid, a copolymer of lactic acid and glycolic acid, or the like had a drawback in that the heat stability, processability, and reproducibility are inferior because the polymerization catalyst is not deactivated in the production of the polymer, and furthermore, the storage stability is also inferior because a monomer formed during the melting acts as a decomposition catalyst of the polymer. If an inorganic powder is melted and is kneaded, together with a conventional lactic copolyester whose polymerization catalyst is not deactivated, a drastic decrease in molecular weight and a drastic increase in monomer formation occurred.

In addition, a conventional bioabsorbable membrane such as polylactic acid or a copolymer of lactic acid and glycolic acid had a drawback in that it was too rigid and too brittle to be used as an absorbable barrier membrane. This drawback has caused further problems in that the absorbable barrier membrane breaks easily when the membrane is implanted into a defective portion in an alveolar bone, tibia, or the like. Furthermore, since a composite material of such a membrane and calcium phosphate is even more brittle, such a composite material could not be used as a barrier membrane in view of its physical properties.

SUMMARY OF THE INVENTION

The objects of the present invention are to provide an absorbable barrier membrane for guided tissue regeneration which is useful for regeneration of animal tissues, including those of humans, the absorbable barrier membrane being superior in heat stability, processability, reproducibility, storage stability, bioabsorbablity, and tissue regeneration effects, and to provide a method for regeneration, using the absorbable barrier membrane, of a mandible, periodontal tissue, or defective tubulous bone, and particularly a defective tubulous bone which possesses a segmental bone defect in which both ends of the bone are in separate segments.

The present inventors have found that a barrier membrane which has suitable elasticity and rapid tissue guiding capability and is superior in processability, reproducibility, and storage stability, may be obtained by using a combined material of a lactic copolyester whose polymerization catalyst is deactivated, and calcium phosphate having a bone guiding capability. Thus, the present invention has been accomplished. That is, the present invention includes:

(1) an absorbable barrier membrane for guided tissue generation, comprising a lactic copolyester in which a polymerization catalyst is deactivated, as an essential component;

(2) an absorbable barrier membrane described in (1), further comprising a calcium phosphate;

(3) an absorbable barrier membrane described in (1) or (2), wherein the polymerization catalyst of the lactic copolyester is one which has been subjected to a deactivation treatment using a chelating agent and/or an acidic ester phosphate;

(4) an absorbable barrier membrane described in any one of (1) to (3), wherein the lactic copolyester contains a structural unit derived from lactic acid and a polyester structural unit derived from dicarboxylic acid and diol, and the content of the polyester structural unit derived from dicarboxylic acid and diol is from 2 to 60% by weight based on the total weight of the lactic copolyester;

(5) an absorbable barrier membrane described in (4), wherein the lactic copolyester endures being folded at least 100 times according to a test for determination of folding endurance.

(6) an absorbable barrier membrane described in any one of (2) to (5), wherein the calcium phosphate is tricalcium phosphate;

(7) an absorbable barrier membrane described in any one of (1) to (5), the membrane having pores of 0.1 to 200 μm in diameter;

(8) an absorbable barrier membrane described in any one of (2) to (7), wherein the lactic copolyester is in the form of a nonwoven fabric;

(9) a method for regeneration of a mandible, comprising use of the absorbable barrier membrane described in any one of (1) to (8);

(10) a method for regeneration of periodontal tissue, comprising use of the absorbable barrier membrane described in any one of (1) to (8);

(11) a method for regeneration of a defective tubulous bone, comprising use of the absorbable barrier membrane described in any one of (1) to (8); and

(12) a method for regeneration of defective tubulous bone described in (11), wherein the defective tubulous bone possesses a segmental bone defect in which both ends of the bone are in separate segments.

The present invention provides an absorbable barrier membrane for guided tissue regeneration which is useful for regeneration of animal tissues, including those of humans, the absorbable barrier membrane being superior in heat stability, processability, reproducibility, storage stability, bioabsorbablity, and tissue regeneration effects, and further provides a method for regeneration, using the absorbable barrier membrane, of a mandible, periodontal tissue, or defective tubulous bone, and particularly a defective tubulous bone which possesses a segmental bone defect in which both ends of the bone are in separate segments.

DESCRIPTION OF THE PREFERRED EMBODIMENTS

Figure 1:
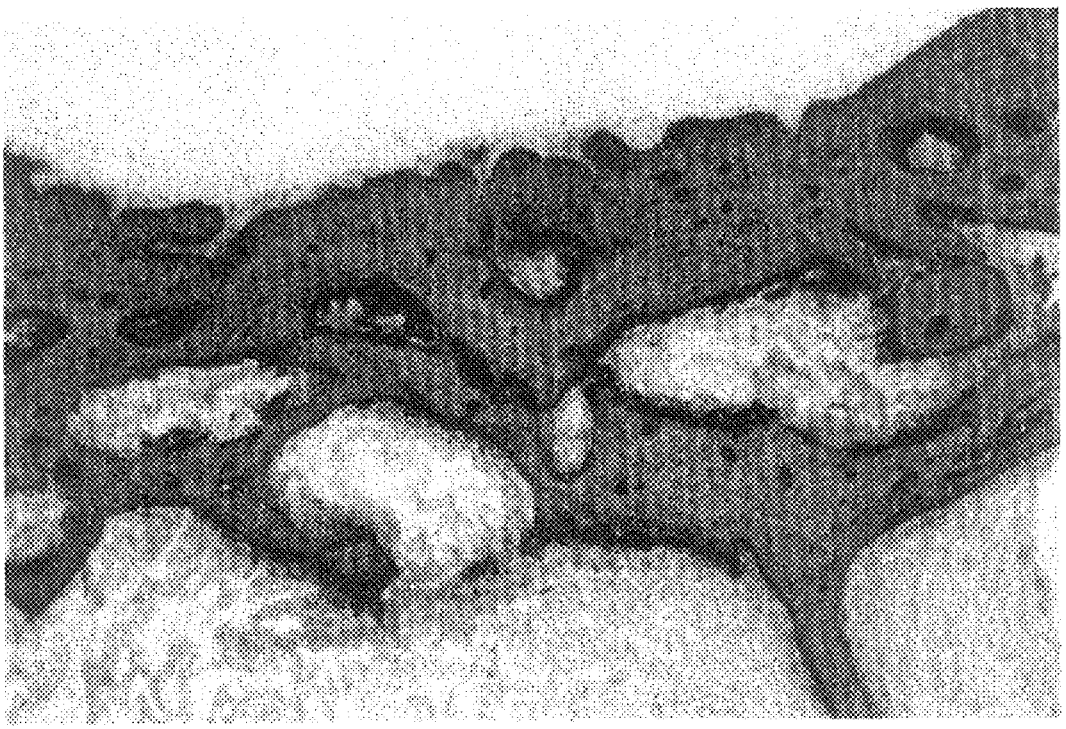
FIG. 1 is a micrograph of a non-decalcified section removed after 12 weeks of a bone regeneration test (Working Example 6) using the absorbable barrier membrane produced in Working Example 1.

Components constituting the absorbable barrier membrane of the present invention will be described hereinafter.

The lactic copolyester used in the present invention is not specifically limited, but specific examples thereof include polylactic acids and copolymers thereof. The copolymers include those having a structure derived from dicarboxylic acid and diol and those prepared by copolymerizing glycolic acid and ε-caprolactone, etc., but these copolymer components may be used alone or in combination.

Generally, when the amount of copolymer component is increased, flexibility increases and strength and stability during kneading are liable to be reduced. However, the lactic copolyester having a structure derived from dicarboxylic acid and diol is particularly superior in strength, kneading properties, and stability to those containing the other copolymer component.

The molecular weight of the lactic copolyester is not specifically limited; however, when the molecular weight is somewhat decreased, strength is liable to be reduced. On the other hand, when the molecular weight is somewhat increased, moldability becomes inferior. Specifically, the weight-average molecular weight is preferably from 20,000 to 400,000, more preferably from 30,000 to 300,000. The term "weight-average molecular weight" used in the present invention refers to a value measured by gel permeation chromatography (relative to a polystyrene standard).

The method for production of the lactic copolyester used in the present invention is not specifically limited, but specifically includes the following methods. In the case of polylactic acid, a method can be used in which ring-opening polymerization of a lactide as a cyclic dimer of lactic acid can be performed in the presence of a ring-opening polymerization catalyst. In the case of the lactic copolyester having a structure derived from dicarboxylic acid and diol, a method can be used in which ring-opening copolymerization and transesterification reaction of a polyester having a structure derived from dicarboxylic acid and diol with a lactide as a cyclic dimer of lactic acid is performed in the presence of a ring-opening polymerization catalyst, or a method can be used in which transesterification reaction of polyester having a structure derived from dicarboxylic acid and diol with polylactic acid is performed.

In addition, the polyester used as a raw material of the lactic copolyester having a polyester structural unit derived from dicarboxylic acid and diol is not specifically limited, but may be any polyester containing a structural unit derived from dicarboxylic acid and diol, and can be obtained by a known method such as dehydration/deglycolation condensation, transesterification reaction and the like.

The diol component as a constituent component of the lactic copolyester having a polyester structural unit derived from dicarboxylic acid and diol is not specifically limited, but specific examples thereof include ethylene glycol, propylene glycol, 1,2-butylene glycol, 1,3-butylene glycol, 1,4-butylene glycol, 2,3-butylene glycol, 1,4-pentanediol, 1,5-pentanediol, 2,4-pentanediol, 1,6-hexanediol, octanediol, neopentyl glycol, cyclohexanediol, xylene glycol, diethylene glycol, triethylene glycol, polyethylene glycol, dipropylene glycol, tripropylene glycol, polypropylene glycol, dibutanediol, polytetramethylene glycol and the like.

The dicarboxylic acid component as a constituent component of the lactic copolyester having a polyester structural unit derived from dicarboxylic acid and diol is also not specifically limited, but specific examples thereof include succinic acid, methylsuccinic acid, 2-methyladipic acid, methylglutaric acid, adipic acid, azelaic acid, sebacic acid, burassylic acid, dodecanedicarboxylic acid, cyclohexanedicarboxylic acid, maleic anhydride, fumaric acid and the like.

The amount of the copolymer component of the lactic copolyester used in the present invention is from 0 to 60% by weight. When the amount is larger than 60% by weight, sufficient strength cannot be obtained. Therefore, it is preferable that the amount be not less than 60% by weight. Since the lactic copolyester contains a structural unit derived from lactic acid and a polyester structural unit derived from dicarboxylic acid and diol, and furthermore, the amount of the polyester structural unit derived from dicarboxylic acid and diol is from 2 to 60% by weight, a membrane having requisite flexibility according to the application portion is obtained. When flexibility is increased, it is easier to connect the membrane to living tissue.

Under these conditions, the lactic copolyester of the present invention containing a polyester structural unit derived from dicarboxylic acid and diol in an amount from 2 to 60% by weight is excellent in flexibility, enduring being folded at least 100 times according to a test for determination of folding endurance.

The absorbable barrier membrane may preferably endure being folded at least 200 times, more preferably at least 400 times, and most preferably at least 1000 times according to a test for determination of folding endurance.

The number of times the absorbable barrier membrane may endure being folded according to a test for determination of folding endurance tends to increase as the content of the polyester structural unit derived from dicarboxylic acid and diol increases. For example, when the content of the polyester structural unit is at a level of 30% by weight, the number of times the absorbable barrier membrane may endure being folded according to a test for determination of folding endurance reaches 1000 times or more.

The term "deactivation treatment of the polymerization catalyst" used in the present invention includes not only deactivation of the polymerization catalyst using a chelating agent or an acidic ester phosphate, but also removal of the polymerization catalyst in the resin after deactivation. By adding the chelating agent and/or acidic ester phosphates in or after the production of the lactic copolyester, the polymerization catalyst used in the production of the lactic copolyester can be deactivated.

When the polymerization catalyst used in the production of the lactic copolyester remains in the lactic copolyester, stability is inferior. Therefore, in the production of a membrane or a combined material of the raw materials, a lactic acid structural unit in the lactic copolyester is regenerated in the form of lactide during heating and molding so that the strength and storage stability of the resulting membrane are reduced. These characteristics are remarkably improved by adding a catalyst deactivator or by removing the polymerization catalyst. The catalyst deactivator chelates normally to the active terminal group in the lactic copolyester and is contained in the lactic copolyester, but may be subsequently removed.

Examples of the polymerization catalyst used in the production of the lactic copolyester include metals (e.g., tin, zinc, lead, titanium, bismuth, zirconium, germanium, cobalt, etc.) known as a transesterification catalyst and compounds thereof, particularly organometallic compounds, carbonates and halides. Among these, tin octanoate, zinc chloride, alkoxy titanium, etc., are preferably used.

The amount of chelating agent and/or acidic ester phosphates used in the present invention varies depending on the kind of catalyst and reaction conditions used in the production of the lactic copolyester, but may be an amount sufficient to deactivate the polymerization catalyst used. Before removing the polymer or during the kneading after completion of the polymerization reaction of the lactic copolyester, the chelating agents and/or acidic ester phosphates are normally added in the amount of 0.001 to 5 parts by weight, preferably 0.1 to 5 parts by weight, based on 1 part by weight of the catalyst used. These chelating agents and/or acidic ester phosphates may also be added to the produced lactic copolyester, followed by kneading.

The chelating agent component used in the present invention is not specifically limited, but specific examples thereof include ethylenediaminetetraacetic acid, ethylenediaminetetraacetic acid disodium salt, oxalic acid, phosphoric acid, pyrophosphoric acid, alizarine, acetylacetone, diethylenetriaminepentaacetic acid, triethylenetetraminehexaacetic acid, catechol, 4-t-butylcatechol, L(+)-tartaric acid, DL-tartaric acid, glycine, chromotropic acid, benzoylacetone, citric acid, gallic acid, dimercaptopropanol, triethanolamine, cyclohexanediaminetetraacetic acid, ditoluoyltartaric acid, dibenzoyltartaric acid and the like. These chelating agent components are particularly preferable as the deactivators used in the present invention.

The acidic ester phosphates used in the present invention are combined with a metallic ion of a catalyst contained in a hydroxycarboxylic copolyester to form a complex, and reduces catalytic activity by exerting effects of inhibiting the polymer chain from cleavage. The "acidic ester phosphates" refer to acidic ester phosphate, ester phosphonate, alkylphosphonic acid, and mixtures thereof. The general formula thereof is shown in the following chemical formula 1.

Chemical formula 1

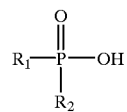

wherein $R_1$ represents an alkyl group or an alkoxyl group, and $R_2$ represents an alkyl group, an alkoxyl group or a hydroxyl group.

In addition, the acidic ester phosphates used in the present invention are acidic ester phosphate, ester phosphonate, alkylphosphonic acid, or mixtures thereof.

Specific examples of acidic ester phosphate include phosphoric acid monomethyl, phosphoric acid dimethyl, phosphoric acid monoethyl, phosphoric acid diethyl, phosphoric acid monopropyl, phosphoric acid dipropyl, phosphoric acid monoisopropyl, phosphoric acid disopropyl, phosphoric acid monobutyl, phosphoric acid dibutyl, phosphoric acid monopentyl, phosphoric acid dipentyl, phosphoric acid monohexyl, phosphoric acid dihexyl, phosphoric acid monoctyl, phosphoric acid dioctyl, phosphoric acid mono-2-ethylhexyl, phosphoric acid di-2-ethylhexyl, phosphoric acid monodecyl, phosphoric acid didecyl, phosphoric acid monoisodecyl, phosphoric acid diisodecyl, phosphoric acid monoundecyl, phosphoric acid diundecyl, phosphoric acid monododecyl, phosphoric acid didodecyl, phosphoric acid monotetradecyl, phosphoric acid ditetradecyl, phosphoric acid monohexadecyl, phosphoric acid dihexadecyl, phosphoric acid monooctadecyl, phosphoric acid dioctadecyl, phosphoric acid monophenyl, phophoric acid diphenyl, phosphoric acid monobenzyl, phosphoric acid dibenzyl, etc., and mixtures thereof.

Examples of ester phosphonate include phosphonic acid monomethyl, phosphonic acid monoethyl, phosphonic acid monopropyl, phosphonic acid monoisopropyl, phosphonic acid monobutyl, phosphonic acid monopentyl, phosphonic acid monohexyl, phosphonic acid monoctyl, phosphonic acid monoethylhexyl, phosphonic acid monodecyl, phosphonic acid monoisodecyl, phosphonic acid monoundecyl, phosphoric acid monotetradecyl, phosphonic acid monohexadecyl, phosphonic acid monooctadecyl, phosphonic acid monophenyl, phosphonic acid monobenzyl, etc., and mixtures thereof.

Examples of alkylphosphonic acid include monomethylphosphonic acid, dimethylphosphonic acid, monoethylphosphonic acid, diethylphosphonic acid, monopropylphosphonic acid, dipropylphosphonic acid, monoisopropylphosphonic acid, diisopropylphosphonic acid, monobutylphosphonic acid, dibutylphosphonic acid, monopentylphosphonic acid, dipentylphosphonic acid, monohexylphosphonic acid, dihexylphosphonic acid, isooctylphosphonic acid, dioctylphosphonic acid, monoethylhexylphosphonic acid, diethylhexylphosphonic acid, monodecylphosphonic acid, didecylphosphonic acid, monoisodecylphosphonic acid, diisodecylphosphonic acid, monoundecylphosphonic acid, diundecylphosphonic acid, monomdodecylphosphonic acid, didodecylphosphonic acid, ditetradecylphosphonic acid, monohexadecylphosphonic acid, dihexadecylphosphonic acid, monooctadecylphosphonic acid, dioctadecylphosphonic acid, monophenylphosphonic acid, diphenylphosphonic acid, monobenzylphosphonic acid, dibenzylphosphonic acid, etc., and mixtures thereof. Since the acidic ester phosphates component has good solubility in organic solvents, the acidic ester phosphates component is superior in workability and reactivity with the lactic copolyester, and exerts good deactivation effects on the polymerization catalyst.

The term "calcium phosphate" used in the present invention refers to those containing a portion derived from phosphoric acid and calcium atoms in a total amount of not less than 50% by weight. Specific examples thereof include tricalcium phosphate, hydroxyapatite, carbonylapatite, magnesium-containing apatite, fluoroapatite and the like. The crystalline structure thereof is not specifically limited; it may be amorphous. Particularly, by using tricalcium phosphate as calcium phosphate, the bone is guided and regenerated more rapidly.

The shape of particles of calcium phosphate is not specifically limited; they may be spherical, porous, or amorphous. The method for production of hydroxyapatite used in the present invention is not specifically limited; specific examples thereof include dry methods, hydrothermal methods, wet methods, and alkoxide methods. A heat treatment may also be performed. The method for production of tricalcium phosphate is also not specifically limited; specific examples thereof include dry methods, hydrothermal methods, and wet methods. A heat treatment may also be performed.

When calcium phosphate exists in a membrane, the stability of the membrane is enhanced and the performance of maintaining the form required as a protective membrane is improved. In addition, the polymerization catalyst is easily deactivated by adding chelating agents and/or acidic ester phosphates to the lactic copolyester. Therefore, when producing a combined material with calcium phosphate by melt-kneading, formation of the lactide is inhibited, and heat stability and storage stability are improved.

The thickness of the absorbable barrier membrane of the present invention is not limited, but is specifically from 0.01 to 2 mm. Those having suitable thickness can be used according to the usage requirements and conditions.

In particular, in the case of using the absorbable barrier membrane in the regeneration of periodontal tissue, the influence on the gum can be reduced by decreasing the thickness of the membrane. In a case where strength is required, the thickness of the membrane may be increased.

The diameter of holes in the absorbable barrier membrane of the present invention is from 0.1 to 200 $\mu$m; this refers to the existence of spaces in the composite material, the space being large enough to accommodate a sphere having a diameter ranging from 0.1 $\mu$m to 200 $\mu$m. The spaces may be replaced with particles of saccharides or salts, biodegradable thread, or the like, which can easily be replaced by a body fluid. Methods for formation of holes is not specifically limited, and examples thereof include laser perforation, stretching and the like.

The shape of pores is not specifically limited; They may be in a thread-like or band-like shape. Those having holes which were naturally formed during the production, such as cloth, nonwoven fabric, etc., may also be used. The pores do not need to be connected to each other or to the outer portion, but they are preferably connected to each other to form a contiguous set of pores, thereby making it possible for a body fluid to penetrate though the contiguous pores, depending on usage. Pores having a diameter of less than 0.1 $\mu$m may exist, and pores having a diameter of more than 20 $\mu$m may also exist. Portions containing no pores may also exist.

By using a membrane comprising a nonwoven fabric of the lactic copolyester and calcium phosphate, invasion of cells undesirable for regeneration of the tissue is inhibited, thereby making it possible to allow flow of body fluid into the tissue. Therefore, the regeneration of the tissue proceeds rapidly. The membrane of the present invention contains drugs such as antibiotics, substance for guiding the tissue and the like. In this case, the drug is slowly released and the effect of these drugs is sustained for a long period of time so that regeneration and repair of the tissue proceeds satisfactorily.

By using the absorbable barrier membrane of the present invention in the curing of marginal parodontitis by guided tissue regeneration, periodontal tissue is rapidly regenerated without removing the membrane because the membrane is superior in processability and can provide suitable elasticity, if necessary. That is, by using the membrane as a membrane for coating a bone defect in the "dental implants placed into sockets intermediately after tooth extraction" for implanting an artificial tooth root immediately after extraction of a tooth, bone neogenesis is facilitated in the vicinity of the artificial tooth root, and it becomes unnecessary to remove the membrane after bone neogenesis.

After extraction of a tooth, by coating the wound after extraction of a tooth with the membrane, downward growth of epithelial and connective tissues in the wound after extraction of a tooth is prevented, and alveolar bone is formed in a form suitable for the wound after extraction of a tooth, thereby making it possible to implant the artificial tooth root in a stable state. It is possible to regenerate bone in a predetermined shape required for each portion, such as the face, etc., by coating the bone defect produced by high absorption of mandible, fracture, extraction of a tumor, perforation of the cranium, traffic accident, etc., with the membrane to form a scaffold for regeneration of bone and guiding the bone. It is also possible to regenerate the bone rapidly by introducing bone pieces formed by comminuted fracture into the portion coated with the membrane. It is also possible to regenerate by using the membrane for the purpose of correction of a mandible or reconnecting peripheral nerves using a tubular membrane.

In the case of application to a segmental bone defect, the portions of the membrane in contact with both bone segments separated by the defect may be tightened by winding with an absorbable thread to fix the membrane to the bone. The bones at both sides of the defect are preferably fixed to each other until the bone is regenerated to yield sufficient strength.

Therefore, the bones can be fixed by using various internal splints known at present or by using an external skeletal fixation device. However, in the case of using an internal splint, those having the same bioabsorbability as that of the absorbable barrier membrane of the present invention are preferably used as an internal splint and screw for fixing the internal splint for the purpose of reducing the burden of removal on the patient. By using the absorbable barrier membrane of the present invention, tubulous bone can be regenerated by guided tissue regeneration and segmented tubulous bone can also be regenerated without using a decalcified bone and without requiring surgery to remove the membrane.

Examples

The following Reference Examples, Working Examples, and Comparative Examples further illustrate the present invention in detail. In the Reference Examples, Working Examples, and Comparative Examples, "parts" are by weight unless otherwise stated.

Storage Stability Test

A 5 cm×5 cm membrane was placed in a thermo-hygrostat (35° C., relative humidity: 80%) and was allowed to stand for 4 weeks. Then, the weight-average molecular weight of the resin component before and after was measured, and a measure of the preservation of the weight-average molecular weight of the membrane was calculated.

Heat Stability Test

A sample was allowed to stand in a vacuum dryer at 200° C. for 30 minutes, and a measure of the preservation of the weight-average molecular weight of the membrane before and after was calculated.

Test for Determination of Folding Endurance by MIT Tester

A sample was pressed at 175° C. so as to prepare a sheet of 250 μm in thickness. A test for determination of folding endurance was conducted on the sheet using an MIT tester according to JIS-P8115.

Processability Test

Using a model of a mandible, a test piece having a required shape was cut from a square sample 10 cm on a side and was bent in a desired shape. Then, a processing operation in the case of treating marginal parodontitis before application was performed and the processability was compared. The processability was evaluated by five ranks in the following sequence, i.e. ⊚ (excellent processability), ○, □, Δ and × (worst processability).

Shape Retention Test

Ease of deformation of a processed membrane having a U-shape by deforming with the fingers at room temperature was evaluated by five ranks in the following sequence, i.e. × (extremely liable to deform), Δ, □, ○ and ⊚ (least liable to deform).

Bone Regeneration Test

Using a mongrel dog, a bone defect (1 $cm^3$) was formed in the mandible. The bone defect was coated with the sample membrane, covered with gum as before and then sutured. After 4, 8, and 12 weeks, the sample was removed and a non-decalcified section (stained with toluidine blue) was made and observed by using an optical microscope (magnification: 40×).

Periodontal Tissue Regeneration Test

Using a mongrel dog, artificial periodontitis was produced by cutting the alveolar bone, periodontal ligament, and cement portion from the periodontal tissue of the second premolar of the mandible 3 mm in thickness×5 mm in depth×3 mm in width to form a cavity. The opening portion of the defect was coated with the membrane. After 12 weeks, the sample was removed and a non-decalcified section (stained with toluidine blue) was made and observed by using an optical microscope (magnification: 40×).

Reference Example 1

To 5 parts of an aliphatic polyester (succinic component: 50% by mol, 1,4-butanediol component: 50% by mol, weight-average molecular weight: 40,000), 95 parts of L-lactide and 15 parts of toluene as a solvent were added and both were melted and mixed under an inert gas atmosphere at 170° C. for 1 hour. After adding 0.03 parts of tin octanoate as a catalyst, the reaction was continued for 4 hours. Then, 0.1 parts of 2-ethylhexyl acid phosphate was added and the reaction mixture was stirred for 30 minutes. When it was taken out, the volatile component was removed through a volatile removing device, followed by cooling and further pelletization. The weight-average molecular weight was 179,000. The molecular weight preservation of the storage stability test was 100%, and that of the heat stability test was 100%. The number of times the sample endured being folded according to a test for determination of folding endurance was 400 (lactic copolyester A).

Reference Example 2

To 30 parts of an aliphatic polyester (sebacic acid component: 50% by mol, ethylene glycol component: 25% by mol, 1,6-hexanediol component: 25% by mol, weight-average molecular weight: 41,000), 70 parts of L-lactide and 15 parts of toluene as a solvent were added and both were melted and mixed under an inert gas atmosphere at 170° C. for 1 hour. After adding 0.03 parts of tin octanoate as a catalyst, the reaction was continued for 4 hours. Then, 0.1 parts of 2-ethylhexyl acid phosphate was added and the reaction mixture was stirred for 30 minutes. When it was taken out, the volatile component was removed through a volatile removing device, followed by cooling and further pelletization. The weight-average molecular weight was 158,000. The molecular weight preservation of the storage stability test was 100% and that of the heat stability test was 100%. The number of times the sample endured being folded according to a test for determination of folding endurance was 1500 (lactic copolyester B).

Reference Example 3

To 30 parts of an aliphatic polyester (sebacic acid component: 50% by mol, ethylene glycol component: 25% by mol, 1,6-hexanediol component: 25% by mol, weight-average molecular weight: 41,000), 70 parts of L-lactide and 15 parts of toluene as a solvent were added and both were melted and mixed under an inert gas atmosphere at 170° C. for 1 hour. After adding 0.03 parts of tin octanoate as a catalyst, the reaction was continued for 4 hours. Then, 1 part of ethylenediaminetetraacetic acid was added and the reaction mixture was stirred for 30 minutes. When it was taken out, the volatile component was removed through a volatile removing device, followed by cooling and further pelletization. The weight-average molecular weight was 161,000. The molecular weight preservation of the storage stability test was 100% and that of the heat stability test was 100%. The number of times the sample endured being folded according to a test for determination of folding endurance was 1500 (lactic copolyester C).

Reference Example 4

To 30 parts of an aliphatic polyester (sebacic acid component: 50% by mol, ethylene glycol component: 25% by mol, 1,6-hexanediol component: 25% by mol, weight-average molecular weight: 41,000), 70 parts of L-lactide and 15 parts of toluene as a solvent were added and both were melted and mixed under an inert gas atmosphere at 170° C. for 1 hour. After adding 0.03 parts of tin octanoate as a catalyst, the reaction was continued for 4 hours. Then, 0.04 parts of tartaric acid was added and the reaction mixture was stirred for 30 minutes. When it was taken out, the volatile component was removed through a volatile removing device, followed by cooling and further pelletization. The weight-average molecular weight was 160,000. The molecular weight preservation of the storage stability test was 100% and that of the heat stability test was 100%. The number of times the sample endured being folded according to a test for determination of folding endurance was 1500 (lactic copolyester D).

Reference Example 5

To 5 parts of an aliphatic polyester (succinic acid component: 50% by mol, 1,4-butanediol component: 50% by mol, weight-average molecular weight: 40,000), 95 parts of L-lactide and 15 parts of toluene as a solvent were added and both were melted and mixed under an inert gas atmosphere at 170° C. for 1 hour. After adding 0.03 parts of tin octanoate as a catalyst, the reaction was continued for 4 hours and the reaction product was taken out, cooled and then pelletized. The weight-average molecular weight was 157,000. The molecular weight preservation of the storage stability test was 42% and that of the heat stability test was 74%. The number of times the sample endured being folded according to a test for determination of folding endurance was 700 (lactic copolyester E).

Reference Example 6

To 30 parts of an aliphatic polyester (succinic acid component: 50% by mol, 1,4-butanediol component: 50% by mol, weight-average molecular weight: 40,000), 70 parts of L-lactide and 15 parts of toluene as a solvent were added and both were melted and mixed under an inert gas atmosphere at 170° C. for 1 hour. After adding 0.03 parts of tin octanoate as a catalyst, the reaction was continued for 4 hours and the reaction product was taken out, cooled and then pelletized. The weight-average molecular weight was 133,000. The molecular weight preservation of the storage stability test was 39% and that of the heat stability test was 68%. The number of times the sample endured being folded according to a test for determination of folding endurance was 2000 (lactic copolyester F).

Reference Example 7

100 parts of L-polylactic acid (manufactured by Purak Co.) was melted by using a laboplasto mixer (manufactured by Toyo Seiki Seisakusho Co., Ltd.) set at 200° C. and 0.1 parts of 2-ethylhexyl acid phosphate was added, followed by kneading. Then, the product was taken out. The number of times the sample endured being folded according to a test for determination of folding endurance was 70 (lactic copolyester G).

Reference Example 8

To a vigorously stirred calcium hydroxide suspension, an aqueous phosphoric acid solution was slowly added dropwise until the pH became 7 and the formed precipitate was calcined at 800° C. for 3 hours to obtain tricalcium phosphate, which was further ground by using a mortar and then passed through a sieve (average particle diameter: 45 $\mu$m) (calcium phosphate A).

Reference Example 9

To a vigorously stirred calcium hydroxide suspension, an aqueous phosphoric acid solution was slowly added dropwise until the pH became 9 and the formed precipitate was calcined at 800° C. for 3 hours to obtain hydroxyapatite, which was further ground by using a mortar and then passed through a sieve (average particle diameter: 39 $\mu$m) (calcium phosphate B).

Working Example 1

40 Parts of a lactic copolyester A and 60 parts of calcium phosphate were kneaded by using a laboplasto mixer (manufactured by Toyo Seiki Seisakusho Co., Ltd.) set at 180° C. for 10 minutes. After taking out the mixture, a membrane having a thickness of 250 $\mu$m was produced by using a hot press and then subjected to a processing test and a shape retention test. The results are shown in Table 1.

Working Example 2

25 Parts of a lactic copolyester B and 75 parts of calcium phosphate were kneaded by using a laboplasto mixer (manufactured by Toyo Seiki Seisakusho Co., Ltd.) set at 180° C. for 10 minutes. After taking out the mixture, a membrane having a thickness of 250 $\mu$m was produced by using a hot press and then subjected to a processing test and a shape retention test. The results are shown in Table 1.

Working Example 3

25 Parts of a lactic copolyester C and 75 parts of calcium phosphate were kneaded by using a laboplasto mixer (manufactured by Toyo Seiki Seisakusho Co., Ltd.) set at 180° C. for 10 minutes. After taking out the mixture, a membrane having a thickness of 250 μm was produced by using a hot press and then subjected to a processing test and a shape retention test. The results are shown in Table 1.

Working Example 4

25 Parts of a lactic copolyester D and 75 parts of calcium phosphate were kneaded by using a laboplasto mixer (manufactured by Toyo Seiki Seisakusho Co., Ltd.) set at 180° C. for 10 minutes. After taking out the mixture, a membrane having a thickness of 250 μm was produced by using a hot press and then subjected to a processing test and a shape retention test. The results are shown in Table 1.

Working Example 5

60 Parts of a lactic copolyester E and 60 parts of calcium phosphate were kneaded by using a laboplasto mixer (manufactured by Toyo Seiki Seisakusho Co., Ltd.) set at 180° C. for 10 minutes. After taking out the mixture, a membrane having a thickness of 250 μm was produced by using a hot press and then subjected to a processing test and a shape retention test. The results are shown in Table 1.

Comparative Example 1

Using a lactic copolyester C, the same operation and test as those described in Working Example 1 were performed. As a result, the processing was not performed because the resulting product was too brittle.

Comparative Example 2

Using a lactic copolyester D, the same operation and test as those described in Working Example 1 were performed. As a result, the processing was not performed because the resulting product was too brittle.

Comparative Example 3

A membrane having a thickness of 250 μm was produced from a lactic copolyester A by using a hot press set at 180° C., and the same test as that described in Working Example 1 was performed. The test results are shown in Table 1.

Working Example 7

Using the absorbable barrier membrane produced in Example 3, a bone regeneration test was performed. As a result, soft tissue was formed after 4 weeks, ossification was recognized after 8 weeks, and the bone had nearly recovered to a normal state after 12 weeks. Abnormalities such as inflammation, etc., were not recognized in the vicinity of the tissue and, at the same time, the absorbable barrier membrane used disappeared by total absorption.

Working Example 8

Figure 2:
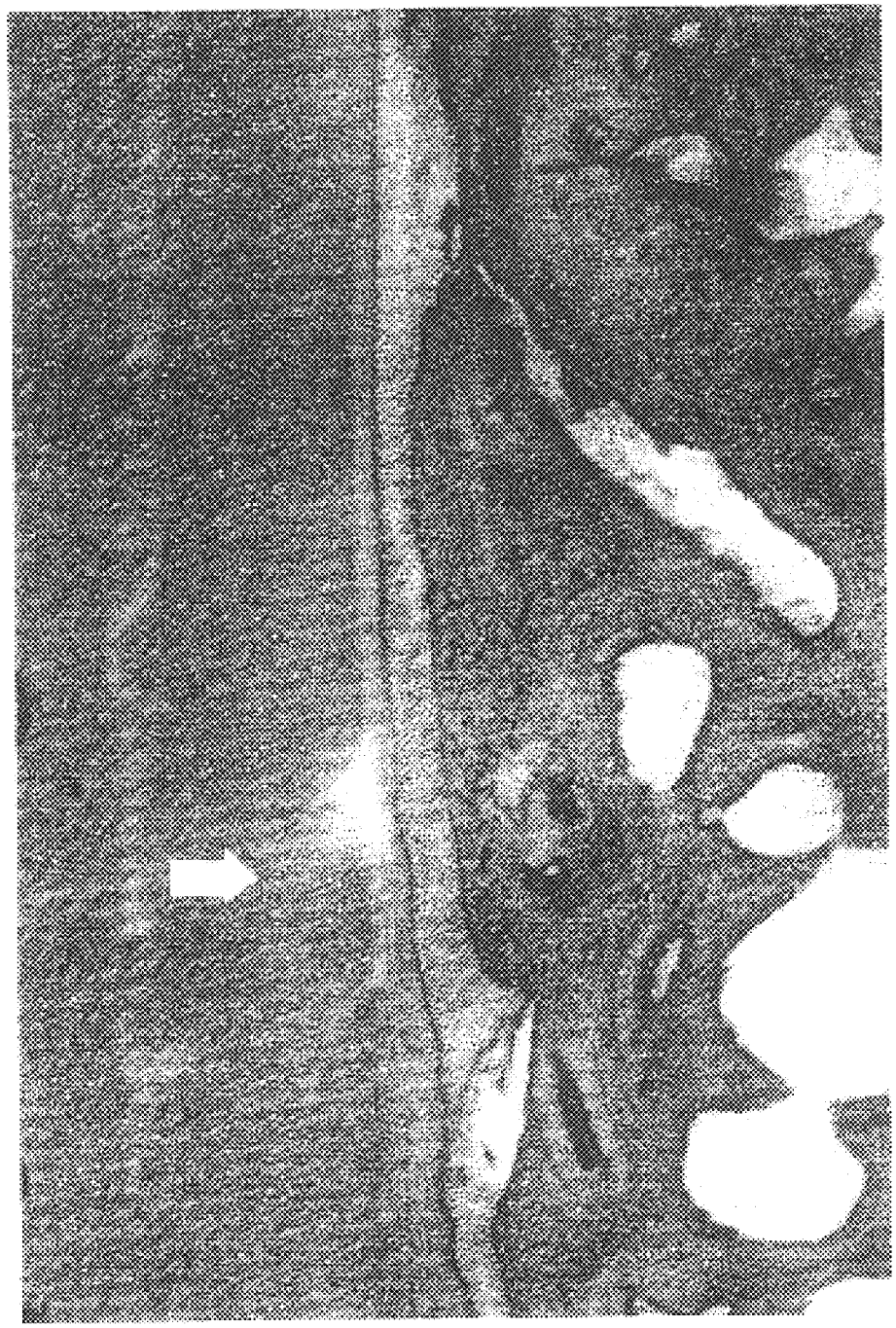
FIG. 2 is a micrograph of a non-decalcified section removed after 12 weeks of a periodontal tissue regeneration test (Working Example 8) using the absorbable barrier membrane produced in Working Example 2.

Using the absorbable barrier membrane produced in Example 2, a periodontal tissue regeneration test was performed. As a result, the periodontal tissue had recovered to a normal state after 12 weeks. A micrograph of a removed non-decalcified section is shown in FIG. 2. A vertical stripe seen in the center of FIG. 2 is a periodontal ligament and the upper portion over the arrow is a position where the defect is produced. It was found that the tissue had nearly recovered in comparison with the untreated tissue at the portion under the arrow. It was also found that the absorbable barrier membrane used disappeared by total absorption. In addition, abnormalities such as inflammation, etc., were not seen in the vicinity of the tissue.

Working Example 9

Using the absorbable barrier membrane produced in Example 4, a periodontal tissue regeneration test was performed. As a result, the periodontal tissue had nearly recovered to a normal state after 12 weeks. Abnormalities such as inflammation, etc., were not seen in the vicinity of the tissue and, at the same time, the absorbable barrier membrane used disappeared by total absorption.

Working Example 10

To 70 parts of a nonwoven fabric using a lactic copolyester B (yarn diameter: 20 μm), 30 parts of calcium phosphate A was adhered and a periodontal tissue regeneration test was performed.

TABLE 1

| | Working Example 1 | Working Example 2 | Working Example 3 | Working Example 4 | Working Example 5 | Comp. Example 6 |
|---|---|---|---|---|---|---|
| Processability Test | ○ | ⊚ | ⊚ | ⊚ | ⊚ | □ |
| Shape Retention Test | ⊚ | ⊚ | ⊚ | ⊚ | ○ | Δ |

Working Example 6

Using the absorbable barrier membrane produced in Working Example 1, a bone regeneration test was performed. As a result, soft tissue was formed after 4 weeks, ossification was recognized after 8 weeks and the bone had nearly recovered to a normal state after 12 weeks. A micrograph of a non-decalcified section removed after 12 weeks is shown in FIG. 1. As is seen from the figure, juvenile bone was regenerated, and regeneration and guiding of the bone were confirmed. It was found that abnormalities such as inflammation, etc., were not seen in the vicinity of the tissue and, at the same time, the absorbable barrier membrane used disappeared by total absorption.

As a result, the periodontal tissue had nearly recovered to a normal state after 12 weeks.

Working Example 11

After external skeletal fixation was applied to tibia of a beagle dog, a segmented bone defect of a length of 10 mm was made so that no periosteum remained. Separately, a bowl made of stainless steel containing a physiological saline was dipped in hot water whose temperature was controlled by using a hot plate. After the physiological saline was heated to about 40° to 45° C., a membrane having a thickness of 200 μm of a lactic copolyester C, which was previously made by using a hot press, was put in the physiological saline and bent in a cylindrical form in accordance with the shape of the bone. The resulting product was applied to the defect. A schematic diagram is shown in FIG. 3.

Figure 3:
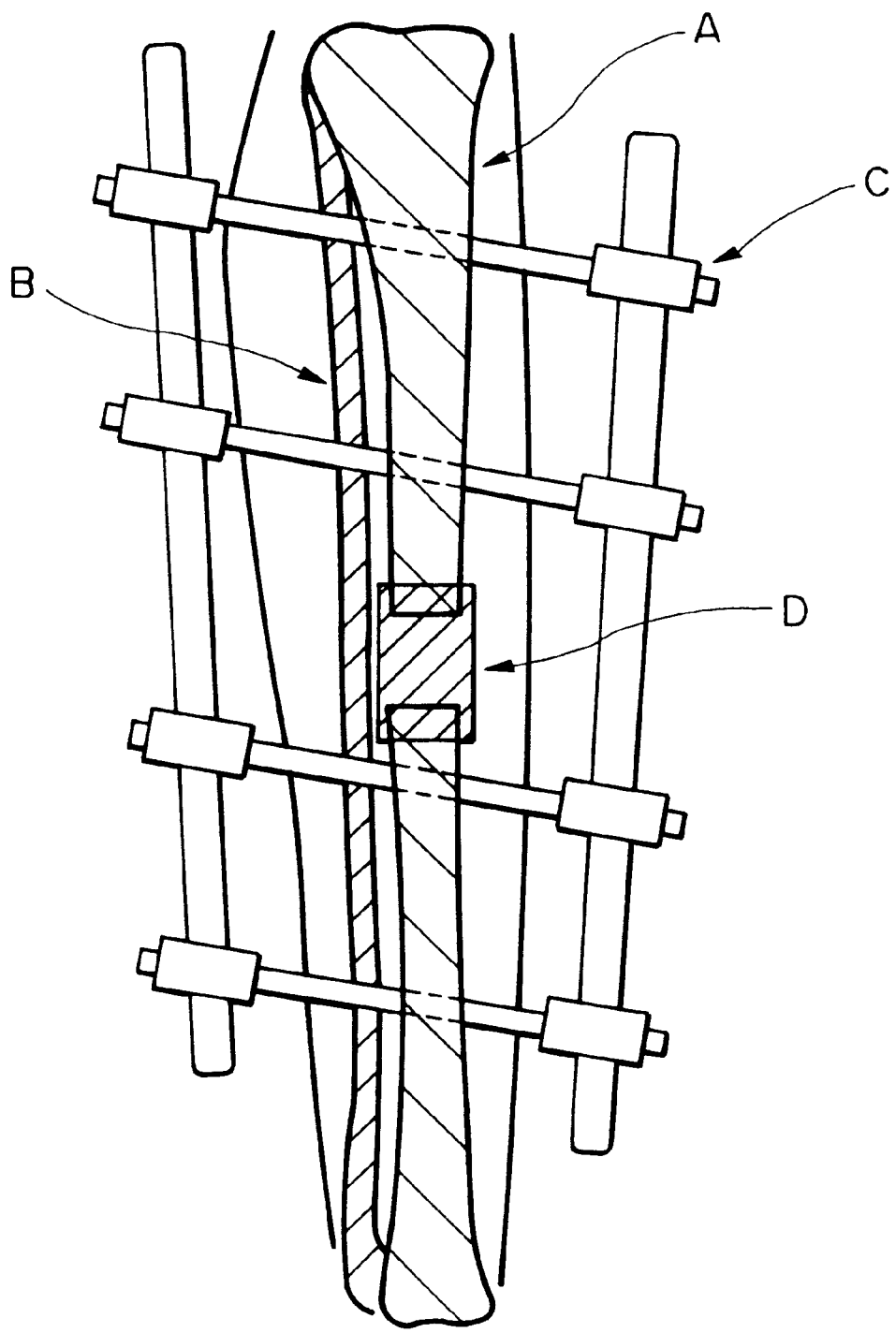
FIG. 3 is a schematic diagram of a regeneration test for a defective tubulous bone which possesses a segmental bone defect in which the bone is separated in two, performed in Working Examples 11 and 12 and Comparative Example 4.

In FIG. 3, A is tibia, B is fibula, C is an external skeletal fixation device, and D is a barrier membrane in the state of being wounded around the bone defect. After completion of the surgery, the muscle and tissue in the vicinity of the defect were sutured as before and recovery after surgery was observed by X-ray examination. As a result, it was confirmed by the X-ray image that calcification of the defect initiated in the state where bone segments at both sides were already connected after 4 weeks, calcification further proceeded after 8 weeks, and the level of calcification almost reached that of neighboring bone tissue, and regeneration of the bone tissue was confirmed by the X-ray image after 12 weeks.

Working Example 12

50 Parts of a lactic copolyester C and 50 parts of calcium phosphate A were kneaded by using a laboplasto mixer (manufactured by Toyo Seiki Seisakusho Co., Ltd.) set at 180° C. for 10 minutes. After taking out the mixture, a membrane having a thickness of 250 μm was produced by using a hot press and then an animal test was performed. After external skeletal fixation was applied to a tibia of a beagle dog, a segmented bone defect of a length of 10 mm was made so that no periosteum remained. Separately, a bowl made of stainless steel containing a physiological saline was dipped in hot water whose temperature was controlled by using a hot plate. After the physiological saline was heated to about 40° to 45° C., a membrane of a composite material was put in the physiological saline and bent in a cylindrical form in accordance with the shape of the bone. The resulting product was applied to the defect in the same manner as in Working Example 11.

The muscle and tissue in the vicinity of the defect were sutured as before. Recovery after the surgery was observed by X-ray examination. As a result, it was confirmed by the X-ray image that calcification of the defect initiated in the state where bone segments at both sides were already connected after 4 weeks, calcification further proceeded after 8 weeks, and the level of calcification almost reached that of neighboring bone tissue, and regeneration of the bone tissue was confirmed by the X-ray image after 12 weeks.

Comparative Example 4

In the same manner as in Working Example 11 except that, after external skeletal fixation was applied to tibia of a beagle dog, a segmented bone defect of a length of 10 mm was made so that no periosteum remained and an absorbable barrier membrane was not wound, the muscle and tissue in the vicinity of the defect were sutured as before. Recovery after the surgery was observed by X-ray examination. As a result, bones at both sides of the defect were not connected.

What is claimed is:

1. An absorbable barrier membrane for guided tissue generation, comprising a lactic copolyester in which a polymerization catalyst is deactivated, as an essential component.

2. An absorbable barrier membrane according to claim 1, further comprising a calcium phosphate.

3. An absorbable barrier membrane according to claim 1, wherein the polymerization catalyst of the lactic copolyester is one which has been subjected to a deactivation treatment using at least one of chelating agents and acidic ester phosphates.

4. An absorbable barrier membrane according to claim 1, wherein the lactic copolyester contains a structural unit derived from lactic acid and a polyester structural unit derived from dicarboxylic acid and diol, and the content of the polyester structural unit derived from dicarboxylic acid and diol is from 2 to 60% by weight based on the total weight of the lactic copolyester.

5. An absorbable barrier membrane according to claim 4, wherein the lactic copolyester endures being folded at least 100 times accordng to a test for determination of folding endurance in accordance with JIS-P8115.

6. An absorbable barrier membrane according to claim 2, wherein the calcium phosphate is tricalcium phosphate.

7. An absorbable barrier membrane according to claim 1, the membrane having pores of 0.1 to 200 μm in diameter.

8. An absorbable barrier membrane according to claim 2, wherein the membrane is a nonwoven fabric comprising lactic copolyester and calcium phosphate.

9. A method for regeneration of a mandible, comprising use of the absorbable barrier membrane of claim 1.

10. A method for regeneration of periodontal tissue, comprising use of the absorbable barrier membrane of claim 1.

11. A method for regeneration of a defective tubulous bone, comprising use of the absorbable barrier membrane of claim 1.

12. A method for regeneration of defective tubulous bone according to claim 11, wherein the defective tubulous bone possesses a segmental bone defect in which both ends of the bone are in separate segments.

* * * * *